United States Patent [19]
Hirsch et al.

[11] Patent Number: 5,391,159
[45] Date of Patent: Feb. 21, 1995

[54] GASTROSTOMY TUBE WITH IMPROVED INTERNAL RETAINING MEMBER

[76] Inventors: William H. Hirsch, 5357 Fortress Trail, Gahanna, Ohio 43230; Donald J. Goldhardt, 1535 Cree Ct., Grove City, Ohio 43123

[21] Appl. No.: 192,229

[22] Filed: Feb. 4, 1994

[51] Int. Cl.⁶ ..................... A61M 5/32; A61M 25/00; A61M 5/00
[52] U.S. Cl. .................... 604/268; 604/271; 604/175; 604/178; 604/278
[58] Field of Search ................. 604/54, 104, 174, 175, 604/268, 271, 275–280

[56] References Cited

U.S. PATENT DOCUMENTS

| | | | |
|---|---|---|---|
| 724,913 | 4/1903 | Montgomery | 604/278 |
| 4,634,435 | 1/1987 | Ingraham | 604/268 |
| 4,758,219 | 7/1988 | Sacks et al. | 604/54 |
| 4,863,424 | 9/1989 | Blake, III et al. | 604/271 |
| 4,944,732 | 7/1990 | Russo | 604/175 |
| 5,007,900 | 4/1991 | Picha et al. | 604/175 |
| 5,074,842 | 12/1991 | Clayton | 604/54 |
| 5,080,650 | 1/1992 | Hirsch et al. | 604/104 |
| 5,112,310 | 5/1992 | Grobe | 604/175 |
| 5,308,325 | 5/1994 | Quinn et al. | 604/264 |

OTHER PUBLICATIONS

Package Insert for "Bard © Guidewire P.E.G. System with Soft Silicone Retention Dome", 1990.

*Primary Examiner*—John D. Yasko
*Assistant Examiner*—Frank Wilkens, III
*Attorney, Agent, or Firm*—Lonnie R. Drayer; Donald O. Nickey

[57] ABSTRACT

An improved gastrostomy tube is a flexible tube having on one inner end thereof an improved energy absorbent internal retaining member which provides for less patient trauma during emplacement and subsequent percutaneous removal, while almost entirely avoiding either separation of the internal retaining member, i.e., the bumper, or its acute displacement. The energy absorbing internal retaining member has a hollow body portion with two resiliently reversible physical forms or shapes, toroidal-like, and, goblet-like connected to a foreshortened hollow axial stem portion that is attached to or integrally made with the inward end of the flexible tube. The internal retaining member is made in the toroidal-like form. During intentional removal, when under pressure against the stomach mucosa, the internal retaining member snaps into the unrolled, goblet-like shape and pulls smoothly out through the stoma tract.

9 Claims, 9 Drawing Sheets

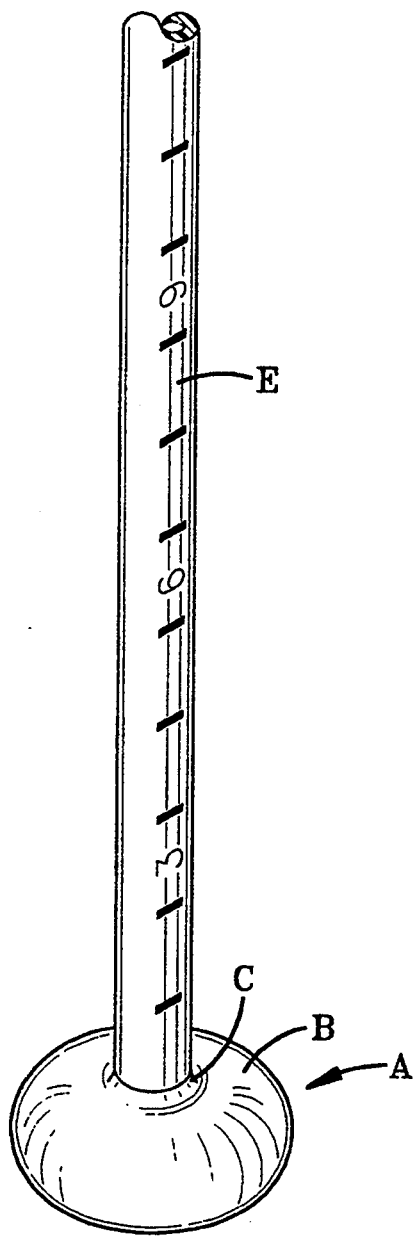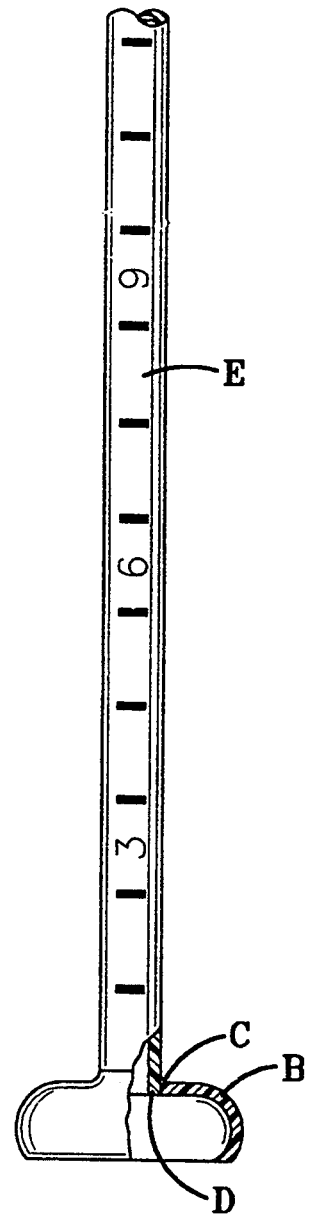
FIG-1
PRIOR ART
FIG-2
PRIOR ART

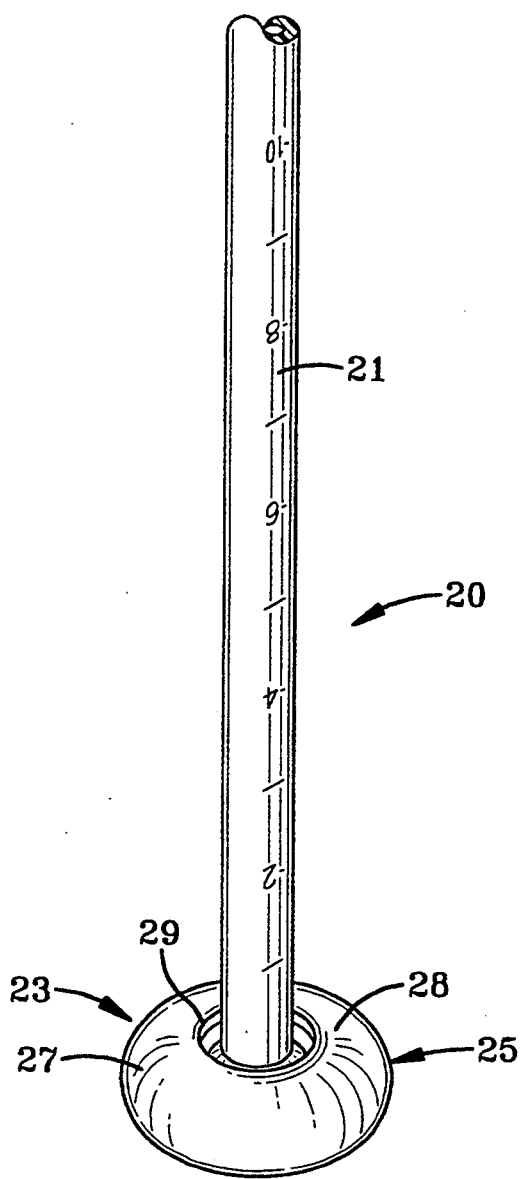
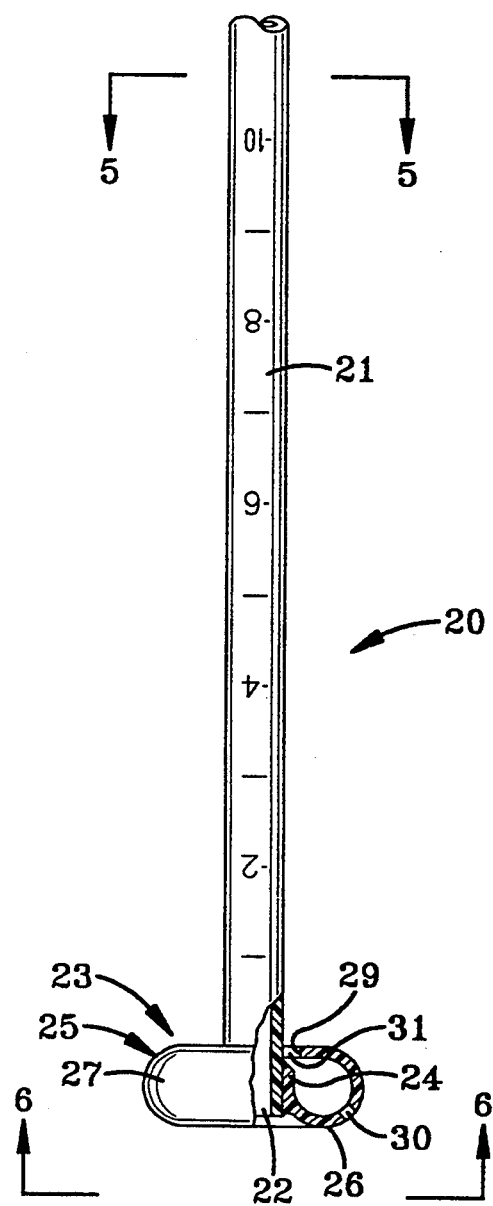
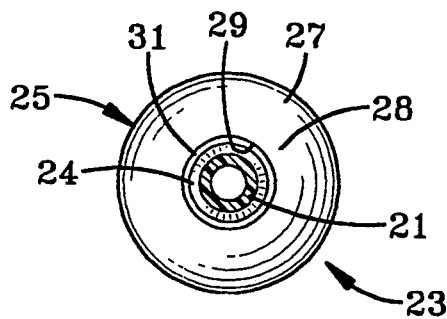
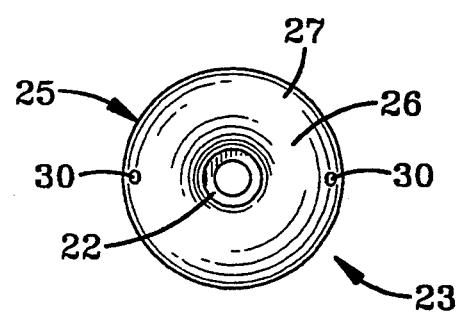
FIG-3   FIG-4
FIG-5   FIG-6

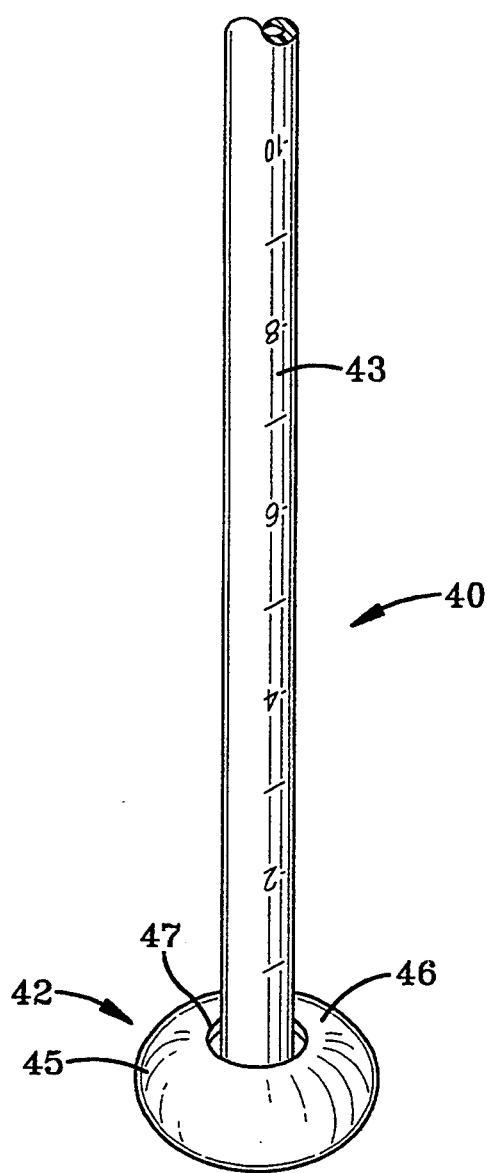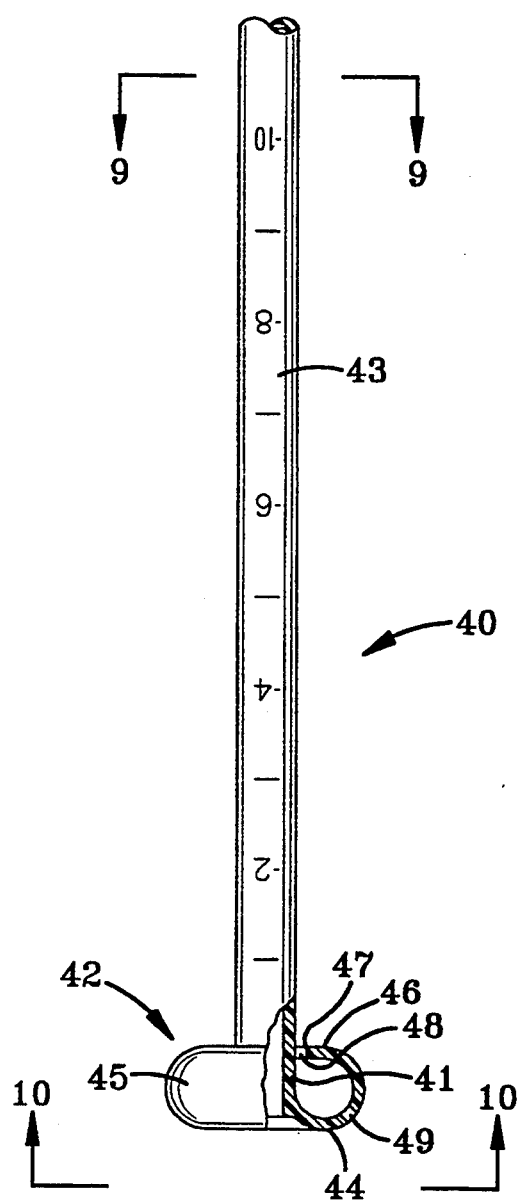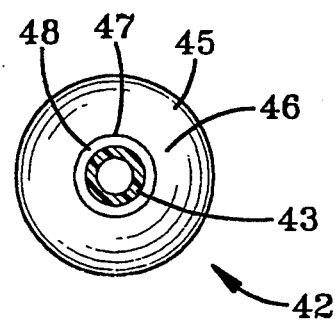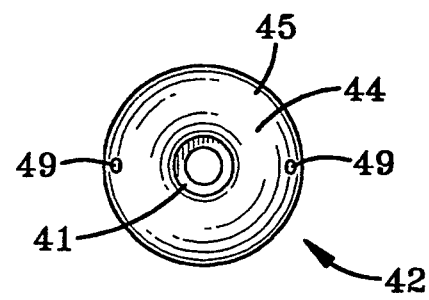
FIG-7    FIG-8
FIG-9    FIG-10

GASTROSTOMY TUBE WITH IMPROVED INTERNAL RETAINING MEMBER

FIELD OF THE INVENTION

The present invention relates to a gastrostomy tube, and more particularly to a gastrostomy tube with an improved internal retaining member, which can be percutaneously removed from a patient without performing an endoscopic procedure.

BACKGROUND OF THE INVENTION

A surgical procedure wherein a passageway is formed through the skin, fascia and stomach wall and a tube installed in the passageway to allow nutrition to be provided directly into the stomach or intestines is known as a gastrostomy. A tube which is inserted through the passageway made during the surgical procedure to maintain the integrity of the passageway and convey fluids therethrough is known as a gastrostomy tube. Examples of individuals who would require such a procedure include: burn patients, whose daily caloric needs are very high; critically ill, weak or comatose patients who may be unable to chew their food; and patients suffering from a diseased or traumatized esophagus, who may be unable to swallow food.

The gastrostomy tube of the present invention is adapted for placement in a patient using the Sacks-Vine procedure, sometimes referred to as a "push" procedure. Briefly, this procedure entails the following steps: (a) passing an endoscope through the esophagus into the stomach; (b) locating a suitable site for the gastrostomy; (c) passing a Seldinger needle through the abdominal wall into the stomach, removing the inner stylet and leaving the cannula in place, then inserting a snare via the endoscope and looping the snare over the end of the cannula; (d) inserting a guidewire through the canula into the stomach, grasping the guidewire via the snare, and withdrawing the endoscope to deliver the guidewire through the mouth; (e) advancing the gastrostomy tube over the guidewire until the gastrostomy tube reaches the cannula and pushes the cannula through the abdominal wall; (f) gently pulling the gastrostomy tube through the abdominal wall until the internal retaining member of the tube engages the gastric mucosa; and (g) securing the gastrostomy tube in place by sliding a retention disc over the portion of the gastrostomy tube which now protrudes through the abdomen of the patient, and then cutting off the excess length of the gastrostomy tube. The Sacks-Vine procedure is well known, and has been described, for example, in the article "A CRITICAL ANALYSIS OF THE SACKS-VINE GASTROSTOMY TUBE: A REVIEW OF 120 CONSECUTIVE PROCEDURES", P. G. Foutch, et al., THE AMERICAN JOURNAL OF GASTROENTEROLOGY, August 1988, pp. 812-815, and books such as ATLAS OF NUTRITIONAL SUPPORT TECHNIQUES, John L. Rombeau, et al., Little Brown and Company, 1989, pp. 132-136.

THE PRIOR ART

U.S. Pat. No. 4,758,219 teaches a gastrostomy tube and an assembly of a dilator and a gastrostomy tube. The internal retaining member is a separate piece of tubing which is affixed such that it extends perpendicularly to the axis of the gastrostomy tube. The internal retaining member of the gastrostomy tube is secured in place by a multi-wing releasable lock formed from the wall of the gastrostomy tube by slitting the tube longitudinally over a predetermined length at a selected number of points about the circumference of the tube. A special instrument must be inserted into the gastrostomy tube to unlock the locking mechanism when the gastrostomy tube is to be removed from the patient, and the short piece of tubing that serves as the internal retaining member is separated from the gastrostomy tube at that time. This prior art device has only the tubular retaining member to seal the stoma against leakage, and will necessarily have a higher contact pressure against the stomach mucosa than the internal retaining member of the gastrostomy tube disclosed herein.

U.S. Pat. No. 5,080,650 teaches another gastrostomy tube and an assembly of a dilator and a gastrostomy tube. This gastrostomy tube has an internal retaining member which has a generally triangular shape with rounded vertices. It is necessary to perform an endoscopic procedure to retrieve the retaining member of the tube when the gastrostomy tube is to be removed from the patient.

A commercially available product known as the Bard TM Guidewire P. E. G. System with Soft Silicone Retention Dome, distributed by C. R. Bard, Inc. of Tewksbury, Mass., U.S.A. provides a gastrostomy tube which may be removed without a surgical or endoscopic procedure by pulling the internal retaining member ("the retention dome") through the stoma tract. However, this prior art gastrostomy tube has been reported to occasionally experience separation of the internal retaining member from the tube member when the gastrostomy tube is removed by pulling the tube through the stoma.

SUMMARY OF THE INVENTION

The gastrostomy tube of the present invention is provided with an improved, energy absorbing internal retaining member of novel design that minimizes patient trauma in everyday use as well as during emplacement and also in the event it is necessary or desired to remove the gastrostomy tube from the stoma of the patient. The novel design of the internal retaining member also provides for reducing the possibility of separation of the internal retaining member, i.e., (sometimes called a bumper), when it is strongly pressed against the stomach mucosa by tension on the gastrostomy tube for any reason while emplaced. This is especially important for percutaneous removal, since separation of the internal retaining member from the tubing requires a subsequent endoscopy for retrieval of the internal retaining member.

The present gastrostomy tube, then, consists primarily of a length of flexible tubing with the novel internal retaining member of flexible material mounted surrounding one end thereof and communicating therewith. The tubing has a first end and a second end. The internal retaining member consists of a foreshortened stem portion that surrounds and is sealingly attached to, or formed with, the end portion of the flexible tubing, and, a hollow body portion that is connected to the stem portion and communicates therewith. The hollow body portion is resiliently and reversibly convertible from a goblet or bowl-like form to a substantially toroidal form, the latter being the particularly energy absorbing form and the form in which the internal retaining member is manufactured and subsequently used when installing the gastrostomy tube. The goblet-like form is the form the internal retaining member takes when the tube is percutaneously removed from the patient.

In goblet-like form, the hollow body portion, which is substantially circular in section at all levels, has a concave base wall that joins and extends away from the stem portion, and quickly and smoothly tapers up to a mid-body section of greatest diameter, and an upper wall that rather quickly tapers back down in diameter and terminates in a rim providing an opening of slightly greater diameter than the stem portion. The concave shape of the base wall is as viewed through the opening in the upper wall.

The shape of the hollow body portion is such that upon inverting, i.e., invaginating, the hollow body portion from a goblet-like form back over the stem portion, the body portion assumes a substantially toroidal form that surrounds the stem portion with the base wall curving out laterally very slightly beyond the first end of the tubing which is overlaid by the stem portion. The first end of the tubing member is the inward end of the gastrostomy tube when in use. The "inner end" of a gastrostomy tube is the end which is located inside the stomach when the gastrostomy tube is emplaced in a patient. The rim of the body portion here is then positioned outwardly of the end of the inward tube, i.e., along the tube away from the inner end of the tube, and normally slightly outwardly of the outward end of the stem portion, depending on the length of stem portion selected.

The gastrostomy tube with its improved internal retaining member is formed of an elastomeric material that is suitable for medical uses, preferably of silicone rubber.

BRIEF DESCRIPTION OF THE DRAWINGS

To acquaint persons skilled in the art with the principles of the invention, a presently preferred embodiment illustrative of the best mode now contemplated for the practice of the invention is described herein making reference to the attached drawings forming a part of the specification and in which drawings:

FIG. 1 is a fragmentary perspective view of a prior art gastrostomy tube;

FIG. 2 is a fragmentary front elevation view, partially broken away and in section, of the prior art gastrostomy tube shown in FIG. 1;

FIG. 3 is a fragmentary perspective view of a gastrostomy tube in accordance with a first embodiment of the present invention;

FIG. 4 is a fragmentary front elevation view, partially broken away and in section, of the gastrostomy tube shown in FIG. 3;

FIG. 5 is a view in section of the gastrostomy tube shown in FIG. 4 taken along line 5—5;

FIG. 6 is a bottom view of the gastrostomy tube shown in FIG. 4 looking in the direction of the arrows 6—6;

FIG. 7 is a fragmentary perspective view of a gastrostomy tube in accordance with a second embodiment of the present invention;

FIG. 8 is a fragmentary front elevation view, partially broken away and in section, of the gastrostomy tube shown in FIG. 7;

FIG. 9 is a view in section of the gastrostomy tube shown in FIG. 8 taken along line 9—9;

FIG. 10 is a bottom view of the gastrostomy tube shown in FIG. 8 looking in the direction of the arrows 10—10;

DETAILED DESCRIPTION OF THE INVENTION

Figure 11:
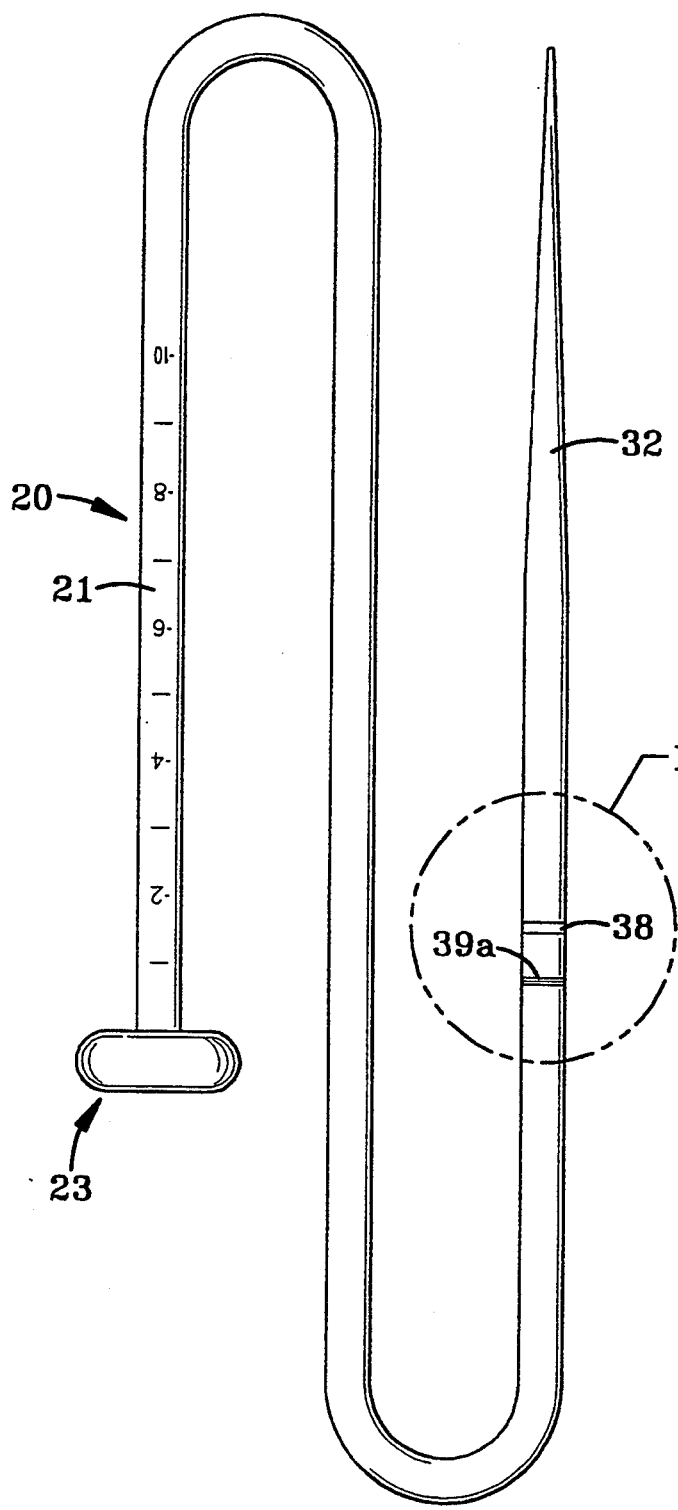
FIG. 11 shows an assembly of a gastrostomy tube, according to either of the embodiments shown in FIGS. 3-10, assembled with a tapered dilator.

Referring to FIGS. 3-6, a first embodiment of the gastrostomy tube of the present invention, indicated generally by the reference numeral 20, is shown to consist mainly of tubular member 21 which is preferably a length of flexible tube having at its first or "inner" end 22 an energy absorbing internal retaining member or bumper 23. The tubular member has a lumen extending longitudinally therethrough.

The terms "inner" and "outer", as used herein with respect to the gastrostomy tube of the invention or parts thereof, are to be understood to be used with reference to the orientation of the gastrostomy tube when emplaced in a patient, inner being in the direction of inside the body of the patient, and outer being in the direction of outside the body.

An important characteristic of the internal retaining member 23, which consists of a foreshortened stem portion 24 joined to and communicating with a toroidal-like body portion 25, is that the body portion is stably reversibly invertible back over the stem portion 24, from a toroidal-like form to a goblet-like form. In other words, there are just two stable physical forms or shapes the body portion 25 will assume, and these forms are mutually reversible with some effort.

Figure 18:
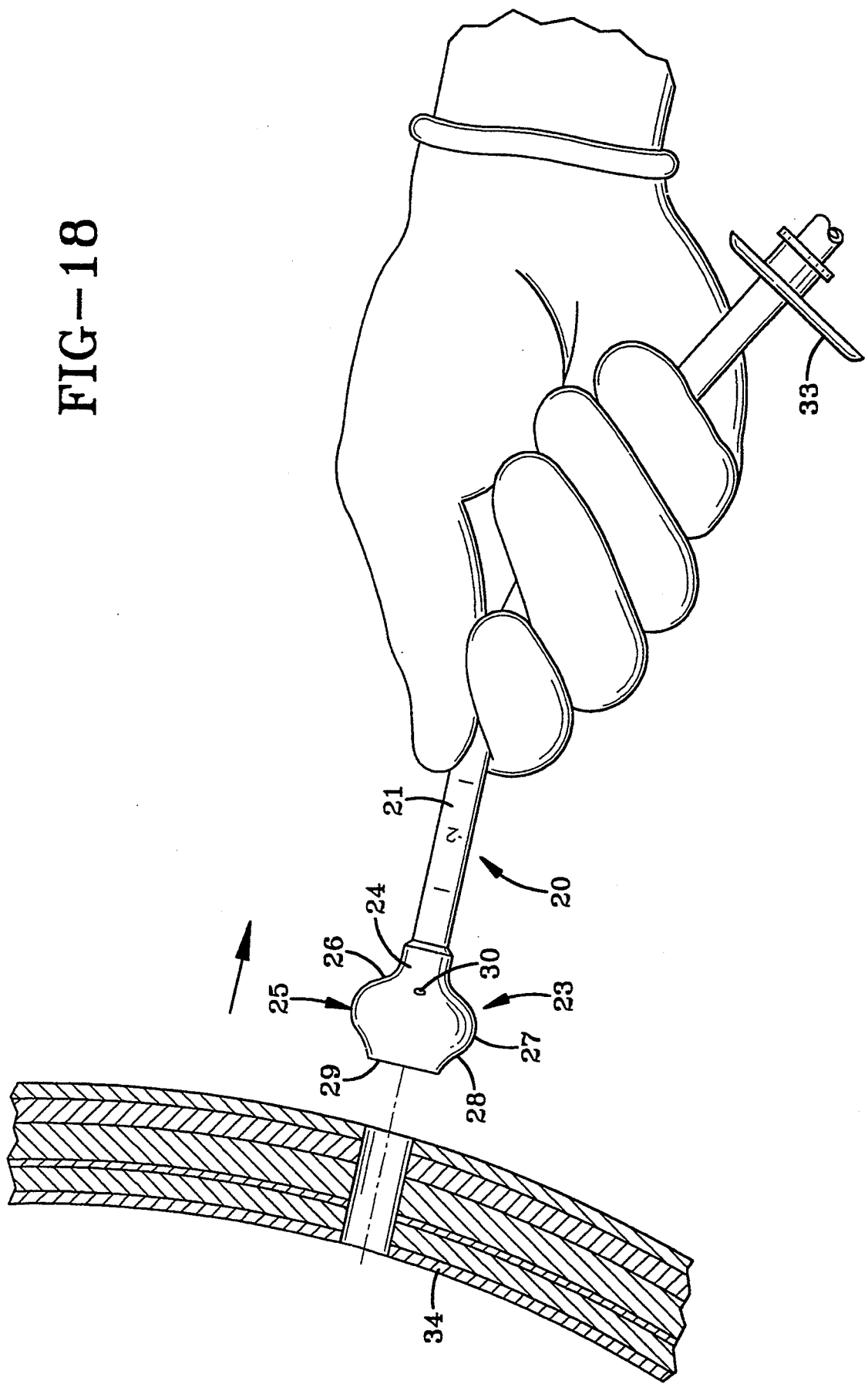

The goblet-like form is illustrated in FIG. 18 where the stem and bowl portions together are in the form of a goblet without a base. The toroidal-like form is illustrated as to the respective embodiments herein described in FIGS. 3 and 4, and in FIGS. 7 and 8. The toroidal-like form is the more effective energy absorbing form and is the form in which the internal retaining member is made and then used during emplacement. The goblet-like form is the form the internal retaining member assumes when the gastrostomy tube of the invention is being withdrawn through the stoma of a patient.

As shown in FIG. 18, wherein the bumper is in goblet-like form, the body portion 25 has a base wall section 26 that is joined to the stem portion 24 and rapidly tapers up to the mid-body section 27 of greatest diameter, from which the upper wall section 28 rapidly tapers down again to a rim 29 defining a circular opening that has a slightly larger diameter than the stem portion 24. Put another way, the diameter of the body portion, as measured perpendicularly to the longitudinal axis of the internal retaining member, when the body portion is in a goblet-like form "tapers up" when it increases and "tapers down" when it decreases. The body wall of the body portion is preferably thinner than the body wall of the stem portion. A suitable thickness for the wall of the body portion is about 0.020 to about 0.030 inch (0.508 to 0.762 mm.)

It is highly desirable that the body portion wall as a whole be shaped so that the substantially toroidal-like form seen in the partial sectional view of FIG. 4 be achieved when the body portion 25 is invaginated over the stem portion 24 from the goblet-like form of FIG. 18. It may be noted that the upper wall portion 28 shown in FIG. 4 does not curl back to form a perfect torus, which would result in the body portion being quite difficult to reverse to the goblet-like form. It is also very desirable to make the opening in the upper wall 28, as defined by the rim 29, somewhat larger than the diameter of the stem portion 24 so that the area of stomach mucosa under the bumper is not blocked and any fluid issuing from the mucosa can drain into the hollow body portion 25. From there, fluids are afforded drainage through at least one drainage hole aperture 30 formed through the base wall section 26 or the mid-body section 27, preferably, adjacent the base wall section 26 as shown in FIGS. 4 and 6. From two to four drainage hole apertures are usable, but two seems to be adequate and preferred for simplicity. The drainage hole aperture or apertures may be spaced radially outward about 0.25 to about 0.375 inch (6.35 to 9.525 mm.) from the longitudinal axis of the internal retaining member when it is in a toroidal-like form. Preferably the drainage apertures(s) are disposed with the center line of the aperture(s) oriented at an angle of about 45° from the longitudinal axis of the tubular member on the side of the side of the internal retaining member which is away from the gap 29, as illustrated in FIGS. 4 and 8.

The spacing 31 of the rim 29 from the stem portion 24 is well illustrated in FIGS. 3, 4 and 5. In practice, the diameter of the rim 29 can be adjusted to achieve a desired degree of resistance to invagination of the body wall to the goblet-like form. A larger diameter of the rim 29 results in less resistance, and a smaller diameter makes the body portion more resistant to invagination. Sufficient resistance is needed to have the internal retaining member effectively prevent unplanned removal of the gastrostomy tube from the patient. The gap also needs to be large enough as a practical matter to remove the core pin of the mold from the internal retaining member during manufacture. The diameter of the rim 29 when the internal retaining member 23 is in a toroidal-like form is suitably about 1.6 to about 1.9 times as great as the diameter of the flexible tube 21 on which the body portion of the internal retaining member is mounted. In an exemplary embodiment, the present gastrostomy tube has a flexible tube about 0.26 inch (6.60 mm.) in outer diameter; the body portion of the internal retaining member while in toroidal-like form is about 0.98 inch (24.9 mm.) in diameter; with the toroidal-like form being about 0.33 inch (8.38 mm.) high. A suitable wall thickness of the body portion is about 0.040 to about 0.060 inch (1.0 to 1.5 mm.). Put another way, it is preferred that the ratio of the largest outside diameter of the internal retaining member in toroidal-like form to the outside diameter of the flexible tubular member is in the range of about 3.4 to about 4.7 to 1. Put yet another way, the diameter of the rim 29 when the internal retaining member is in a toroidal-like form, is about 1.6 to about 1.9 times as great as the outside diameter of the tubular member. Of course, these dimensions may be varied somewhat to accommodate the needs of patients with various thicknesses and conditions of the abdominal wall.

Referring again to FIG. 4, the stem portion 24 of the internal retaining member 23 is shown attached to and sealingly surrounding the first or inward end 22 of the flexible tube 21. The attachment may be made by insert molding of the elastomeric material to form the parts, positioning the flexible tube in a mold and then injecting polymer into the mold and polymerizing it to make the internal retaining member. The internal retaining member and flexible tube may also be preformed separately and then attached together using an adhesive, but the attachment tends to be not as strong and reliable as that achieved by insert molding. The length of the stem portion 24 is ordinarily about the axial width of the toroidal-like form body section 25 that surrounds it. In any event, the length of the stem portion should be long enough to permit a strong bond to the flexible tube 21.

Turning now to FIGS. 7-10, a second embodiment of the gastrostomy tube of the present invention, indicated generally by the reference numeral 40, is shown to have the stem portion 41 of the internal retaining member 42 integrally formed with the tubing member 43. The construction is strong and reliable, but the difficulty and expense of manufacturing makes this type of construction less preferred than the insert molded type, while the strength and reliability make it more preferred, ordinarily, to the adhesive bonded bumper attachment.

In all other respects, the second embodiment is the same as the first embodiment in the shaping and spacing of the base wall section 44, the mid-body section 45, the upper wall section 46, the rim 47 and the spacing 48 of the rim 47 from the stem portion 41. Also, the same considerations obtain as described above for the drainage aperture holes 49.

One of the gastrostomy tubes herein described, such as tube 20 in FIG. 3, is readied for emplacement by attaching it to a tapered dilator 32 having a lumen extending longitudinally therethrough, as shown in FIG. 11, prior to passing it, dilator first, over a guidewire according to a procedure such as that described in the background discussion above.

Figure 12:
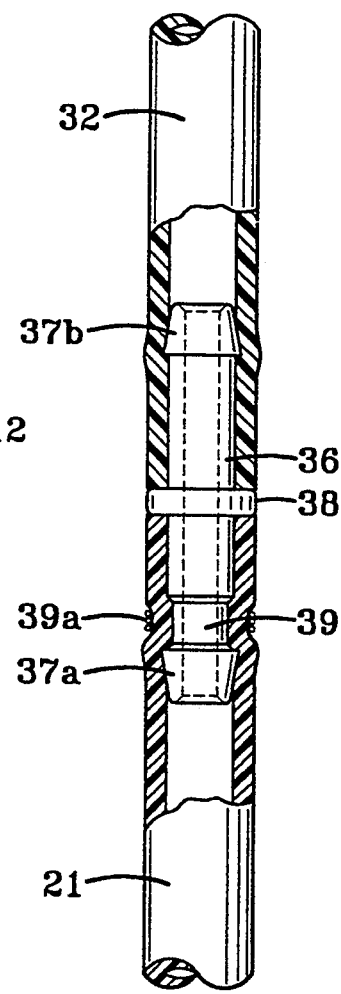
FIG. 12 is an enlarged fragmentary view in front elevation, partially broken away and in section, of the connection of the gastrostomy tube to the tapered dilator shown in FIG. 11.

The details of a suitable connection to the dilator 32 are shown in FIG. 12 which is an enlarged fragmentary view, partly broken away and in section, of the area of the connection. Here the means for the connection includes a rigid tubular connector member 36, normally of polymeric material such as a nylon, that fits into the opposed ends of both the gastrostomy tube 21 and the dilator tube 32. The connector member 36 is a straight tube with a so-called barb 37a, 37b at each end and a radially extending flange or boss 38 about at midlength. The flange 38 serves as a stop against which the second end of the gastrostomy tube and the larger diameter end of the dilator are pushed when connection is made between them. Each barb 37a, 37b consists of a tapered end section of the tubular connector member 36, the taper along the axial direction being from a slightly smaller outer diameter than the rest of the connector member at the very end thereof to a slightly larger diameter with a rather sharply defined end to the tapered section which serves to resist slippage back out of the lumen into which it is inserted. The connector member here shown has a slightly smaller outer diameter section 39 adjacent barb 37a. A length of suture 39a is ordinarily wrapped around the exterior of the gastrostomy tube 21 concentrically to smaller outer diameter section 39 and tied snugly to secure the connector member 36 to the gastrostomy tube 21. The suture 39a is preferably coated with a suitable adhesive to fill-in the depression in the tubular member caused by the suture.

Figure 13:
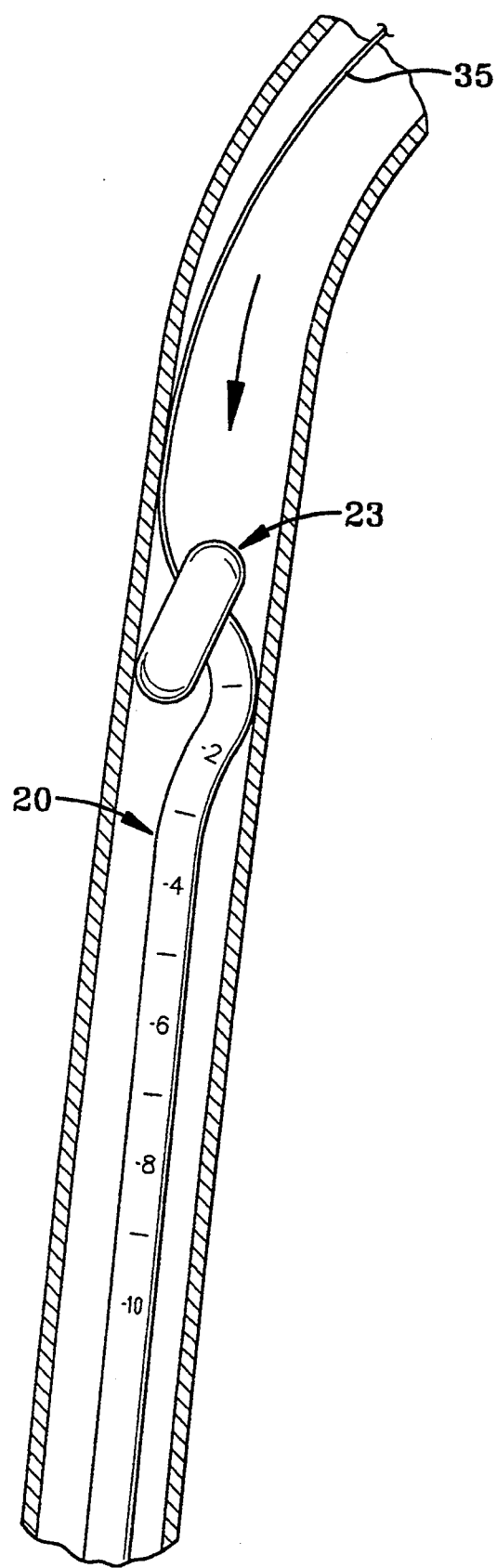
FIG. 13 shows the normal orientation of the gastrostomy tube of the invention while being passed over a wire and through the esophagus of a human patient.
Figure 14:
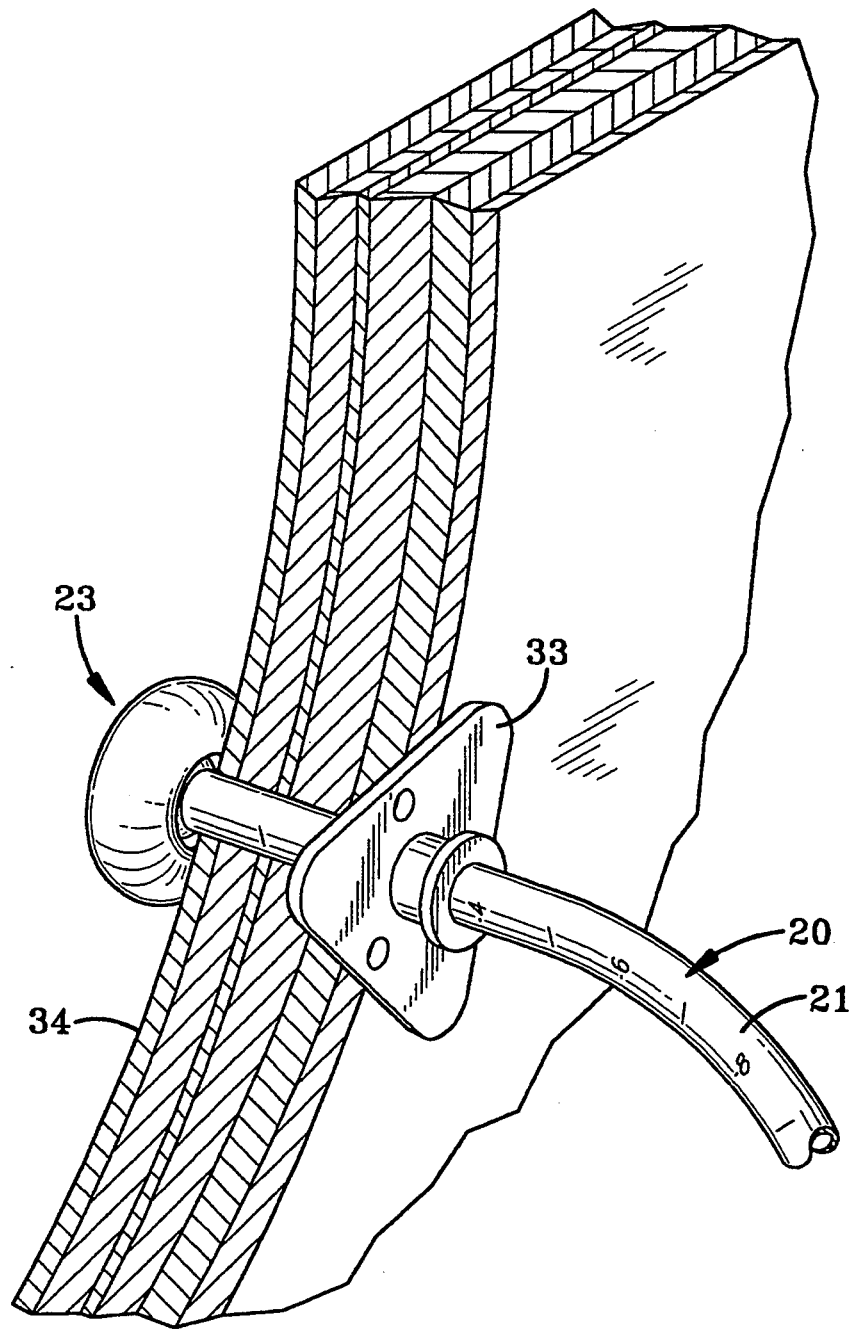
FIG. 14 shows a gastrostomy tube of the present invention installed in the stomach of a human patient.

Referring next to FIG. 13, in pulling the gastrostomy tube 20 with its bumper, i.e., internal retaining member, over a guidewire 35, the gastrostomy tube initially is drawn down through the esophagus during a placement procedure of the type described above in the background section. As shown in FIG. 13, the gastrostomy tube of the invention assumes an orientation with the internal retainer member 23 canted over at an angle that permits rather gentle passage with minimized resistance to forward movement. The dilator 32 and the attached gastrostomy tube 20 are then drawn on into the stomach and over to the cannula. After the dilator 32 has followed the cannula through the abdominal wall, a gentle pull is exerted to also bring the gastrostomy tube through the stoma until the internal retaining member 23 is up against or closely adjacent to the stomach mucosa 34 as seen in FIG. 14. An exterior retaining member 33 is then slipped over the dilator tube 32 and down the connected flexible tubular member 21 of the gastrostomy tube 20 towards the stoma until the external retaining member 33 is in contact with the abdominal skin around the stoma. The dilator 32 is then disconnected and excess flexible tubing 21 is trimmed off and suitable connection made to any source of fluids to be injected.

Figure 16:
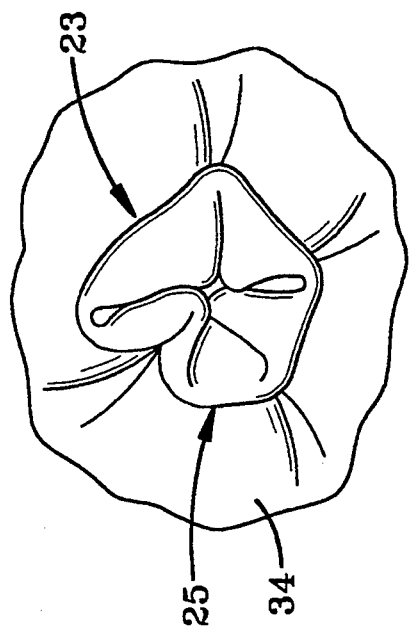
FIGS. 15-18 illustrate the percutaneous removal of a gastrostomy tube of the present invention from the stomach of a human patient.
Figure 15:
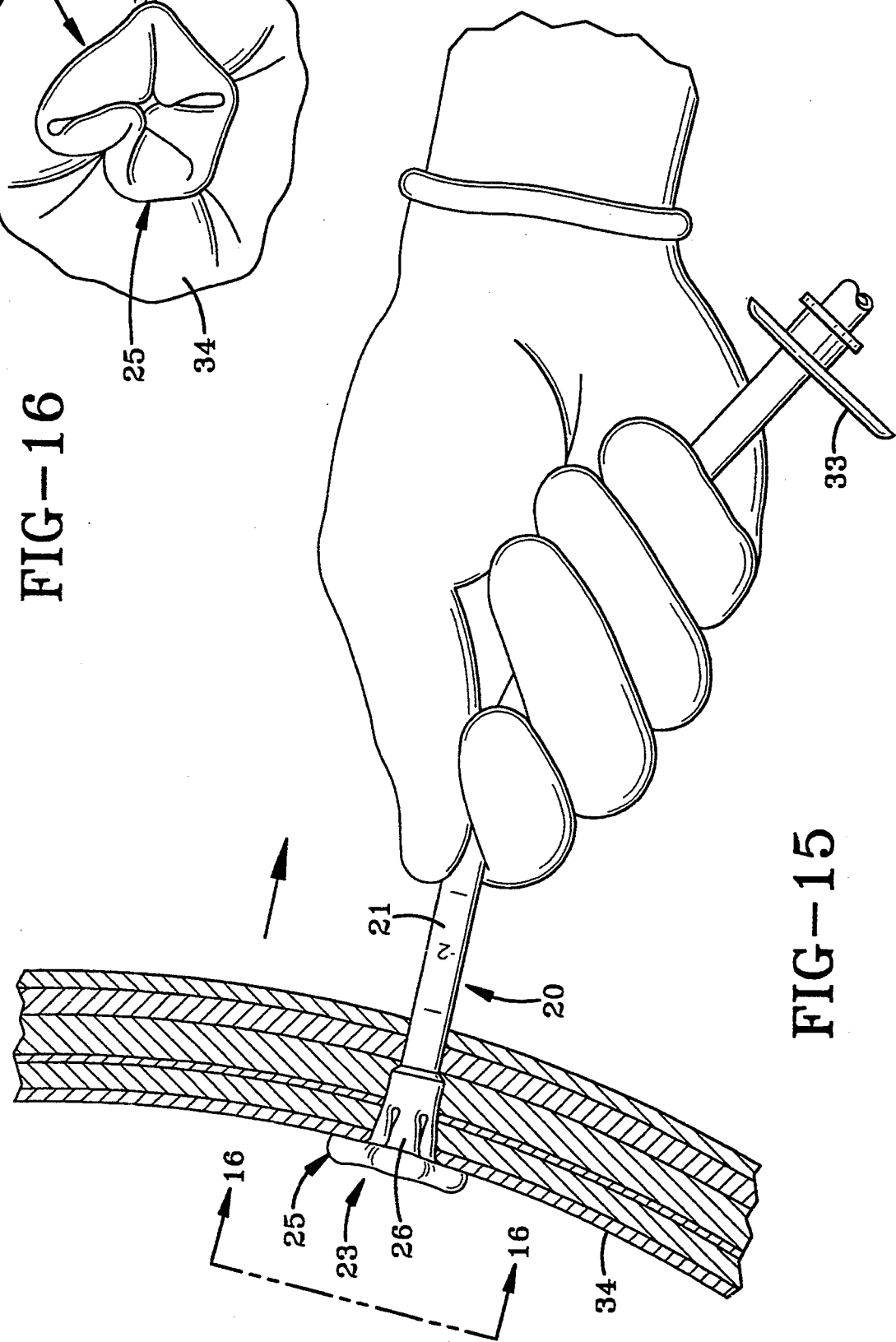
Figure 17:
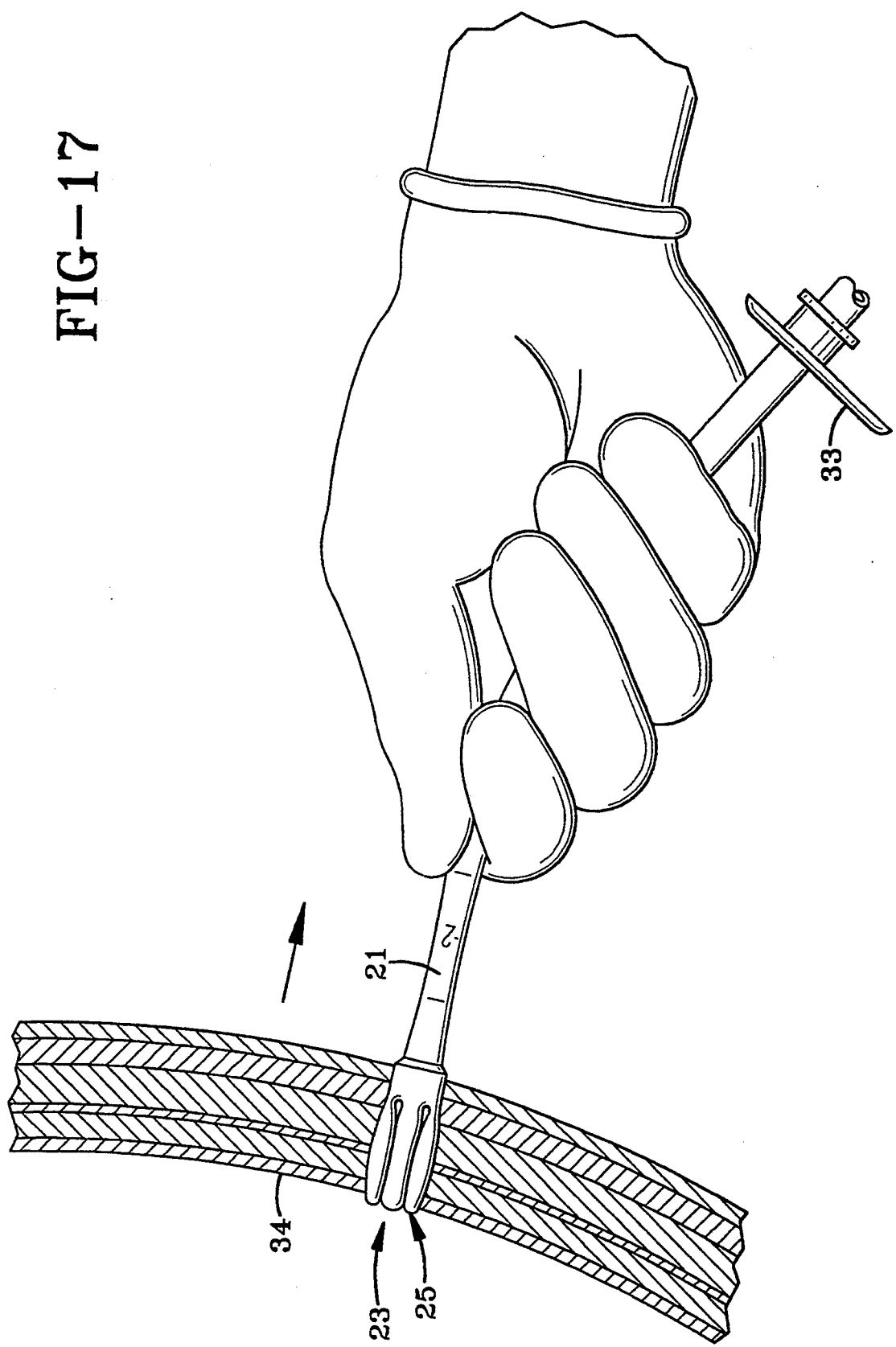

The behavior of the present gastrostomy tube with its improved energy absorbing internal retaining member is more clearly understood with reference to FIGS. 15-18. In FIG. 15 the external retaining member 33 has been moved out of the way and the tubular member 21 has been grasped for the purpose of removing the gastrostomy tube and pull is being exerted, commencing to narrow down the base wall section 26 of body portion 25 of the energy absorbing internal retaining member 23, and also narrowing the axial width of the toroidal-like form of the mid-body section 27. In FIG. 16, which is a view from inside the stomach, there is illustrated the body portion 25 now in invaginated form to the goblet-like form and being folded together as it enters the Stoma in the stomach mucosa 34. In FIG. 17 the folded body portion 25 is seen passing through the stoma with minimal trauma to the patient. In FIG. 18 there is shown the emergent internal retaining member with the body portion in the goblet-like or bowl-like form.

As seen in FIGS. 1 and 2, the prior art gastrostomy device there shown differs from that of the present invention in having a bumper A of inverted shallow open bowl, or bell, form with a substantially flat base wall B joined by a very short stem portion C to an end D of the flexible tube E. The shallow bowl form is believed to give rise to critically large radially directed forces within the stoma during intentional removal of such a prior art gastrostomy tube from the stoma of a patient. The radially directed forces result in greater patient trauma. Another problem that this form of gastrostomy tube is subject to is acute displacement. If removal is not intentional and carefully attended for complete removal, the open bowl form of bumper with attendant radially directed forces when it is forced to partially fold during transit of the stoma tract, may occasionally lodge between and damage or spread apart layers of the friable fibrous tract forming the stoma. The adverse consequence of this is likely to be that if the condition is not noted and an attempt is made to inject a fluid through the gastrostomy tube, the fluid may force its way between layers of the exposed stoma tract and enter the peritoneum. Or, stomach fluids may find their way between layers of the exposed stoma tract and enter the peritoneum. Further, the short area afforded for bonding of the stem portion C to the flexible tube E makes the prior art device more subject to separation of the internal retaining member, i.e., the bumper.

A very important difference in mode of action of the internal retaining member of the present gastrostomy tube as compared to the prior art device lies in the fact, then, that the internal retaining member of the prior art device elongates until it reduces in diameter to the critical diameter, whereupon it collapses in the radial direction and enters the stoma, meanwhile constantly exerting force in the outwardly radial direction against the various layers in the stoma tract with considerable tendency for the internal retaining member to try to assume its flat bowl shape with resulting damage to the stoma tract.

The internal retaining member of the present invention does not need to elongate markedly initially, but instead, reverses form to the goblet or bowl-like configuration in a snap-like action while still within the stomach lumen, whereupon the outwardly radially directed forces are greatly diminished, resulting in minimal trauma to the patient during withdrawal through the stoma. By proper selection of the diameter of the rim 29, taking into account the tensile strength of the elastomeric material of which the device is formed, the desired resistance to the snap-like reversal of form can be obtained so that the improved internal retaining member nonetheless performs very satisfactorily as a retaining member.

Laboratory testing in which the gastrostomy tube of the present invention and the prior art device were each drawn through a simulated stoma tract with pressure sensors mounted within it have shown that the radially directed forces exerted by the improved internal retaining member of the gastrostomy tube of the present invention are from about 25 to 50 percent smaller, and generally about 25 to 35 percent smaller than the radially directed forces exhibited by the prior art device of FIGS. 1 and 2.

Experiments carefully conducted upon swine on each of which a gastrostomy had been performed, showed that the internal retaining member of the gastrostomy tube of the present invention changed shape from the toroidal-like form to the goblet-like form before entering the stoma tract during percutaneous, non-endoscopic removal of the gastrostomy tube. As a result, the internal retaining member ordinarily pulled through the stoma tract of the subject animals smoothly.

What is claimed is:

1. A gastrostomy tube comprising:
(a) a flexible tubular member, with a first end and a second end, and (b) a hollow energy-absorbing internal retaining member; the internal retaining member having a foreshortened stem portion and a body portion; the stem portion surrounding the first end of the tubular member and being sealingly attached thereto;
the body portion being substantially toroidal-like in form and substantially concentrically surrounding the stem portion and being connected thereto and having at least one drainage hole aperature formed therethrough radially outwardly from the stem portion;
the body portion having two stable resiliently reversible physical configurations, the toroidal-like form and a goblet-like form, the toroidal-like form being invaginatable to the goblet-like form and vice versa, the body portion when in toroidal-like form is concentric with and surrounds the stem portion and has a base wall curving out laterally beyond the first end of the tubular member and curling back towards itself to a rim which is disposed radially outwardly of the stem portion and defines a circular apperature which allows the body portion to be invaginated to the goblet-like form.

2. The gastrostomy tube of claim 1 in which the internal retaining member in goblet-like form is shaped substantially like a goblet without a base, with the base wall of the body portion having a hollow bowl shape and being integrally formed with the foreshortened hollow stem portion communicating therewith; the bowl-shaped body portion opening away from the first end of the tubular member; the bowl-shaped body portion having a base section joined to the stem portion, and a mid-body section, with the middle part of the mid-body section having a substantially larger diameter than the rim;

the base wall of the bowl-shaped body portion being invaginatable back over the stem portion to take the substantially toroidal-like form concentric to the stem portion;

the body portion showing snap-like behavior when forced from the toroidal-like to the goblet-like form.

3. The gastrostomy tube of claim 1 in which the ratio of the largest outside diameter of the internal retaining member in toroidal-like form to the outside diameter of the flexible tubular member is in the range of about 3.4 to about 4.7 to 1.

4. The gastrostomy tube of claim 1 in which the diameter of the rim when the internal retaining member is in the toroidal-like form, is about 1.6 to about 1.9 times as great as the outside diameter of the tubular member.

5. The gastrostomy tube of claim 4 in which the tubular member is about 0.26 inch in external diameter and the internal retaining member in toroidal-like form is about 0.98 inch in outside diameter and about 0.33 inch high.

6. The gastrostomy tube of claim 1 in which the number of drainage hole aperatures in the body portion is two to four.

7. The gastrostomy tube of claim 1 in which the stem portion of the internal retaining member is insert molded to the first end of the tubular member.

8. The gastrostomy tube of claim 1 in which the stem portion of the internal retaining member is integrally formed with the first end of the tubular member.

9. The gastrostomy tube of claim 1 in which the internal retaining member is injection molded and then the stem portion is adhesively bonded to the first end of the tubular member.

* * * * *